United States Patent [19]  [11]  4,155,934
Kalopissis et al.  [45]  May 22, 1979

[54] HAIR DYE COMPOUNDS

[75] Inventors: Gregoire Kalopissis, Paris; Andree Bugaut, Boulogne-sur-Seine, both of France

[73] Assignee: L'Oreal, Paris, France

[21] Appl. No.: 550,583

[22] Filed: Feb. 18, 1975

Related U.S. Application Data

[60] Division of Ser. No. 70,480, Sep. 8, 1970, Pat. No. 3,904,690, which is a continuation-in-part of Ser. No. 598,179, Dec. 1, 1966, Pat. No. 3,560,136.

[51] Int. Cl.$^2$ ............................................. C07C 87/68

[52] U.S. Cl. ...................... 260/567.6 M; 260/567.6 P
[58] Field of Search ..................... 260/567.6, 567.6 N, 260/567.6 M

[56] References Cited

U.S. PATENT DOCUMENTS 3,431,304  3/1969  Fryer et al. ........................ 260/570

Primary Examiner—James H. Reamer
Attorney, Agent, or Firm—Brisebois & Kruger

[57] ABSTRACT

Substituted nitrophenylene-diamine quaternary ammonium salt hair dye compounds.

4 Claims, No Drawings

HAIR DYE COMPOUNDS

SUMMARY OF THE DISCLOSURE

This application is a division of application Ser. No. 70,480, filed Sept. 8, 1970 now U.S. Pat. No. 3,904,690 which was a continuation-in-part of application Ser. No. 598,179, filed Dec. 1, 1966 now U.S. Pat. No. 3,560,136.

Products formed from nitrophenylene-diamine by substitution are well known active ingredients used in solutions for coloring keratinic fibers, and particularly human hair.

In order to broaden the range of shades which may be obtained, resort has been had to dyes derived from nitroparaphenylene-diamine or nitro-ortho-phenylene diamine by attaching to at least one of the amine groups connected to the aromatic nucleus, a group, such as an alkyl chain, comprising an extra nuclear amine function. Dyes have also been used in which the amine groups connected to the aromatic nucleus were substituted by alkyl or hydroxyalkyl radicals.

The series of derivatives produced from nitroparaphenylene-diamine makes it possible to obtain colors ranging from red to blue; the series produced from nitro-ortho-phenylene diamine makes it possible to obtain orange shades.

Since in practice natural hair shades are obtained by mixing dyes ranging from yellow to blue, it is most important to have hair dyes producing a yellow or yellow-green shade available.

It is the object of this invention to provide yellow dyes having a good affinity for keratinic fibers.

Specifically, it is the object of this invention to provide a new article of manufacture which consists of a water soluble compound which may be used as a dye and has the following formula:

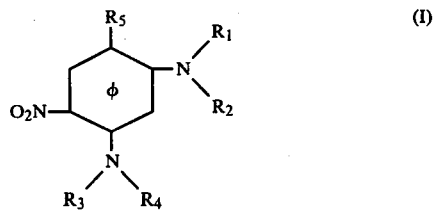

(I)

in which $R_1$, $R_2$, $R_3$, $R_4$ represent an atom of hydrogen, a lower alkyl radical having 1–4 carbon atoms, or a radical corresponding to the formula:

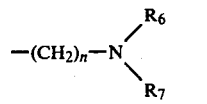

in which $R_6$ and $R_7$ represent a hydrogen atom or a lower alkyl radical having 1–4 carbon atoms and may form part of a heterocyclic ring such as morpholino and piperdino, but $R_6$ and $R_7$ may not represent a hydrogen atom when they are on a substituent chain of the nitrogen atom in the para position with respect to the $NO_2$, n represents a whole number between 2 and 6 inclusive, only one of the radicals $R_1$, $R_2$, $R_3$ and $R_4$ representing a radical

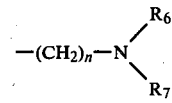

and $R_5$ representing a hydrogen atom, lower alkyl radical having 1–4 carbon atoms, a halogen atom or a lower alkoxy radical having 1–4 carbon atoms.

The invention also relates to those quaternary derivatives of the compositions according to formula (I) by quaternization of the extra-nuclear amine group at the end of the chain, when said group is a tertiary amine group.

The present invention is also directed to a process for preparing one category of chemical compositions covered by general formula (I) and represented by general formula (II):

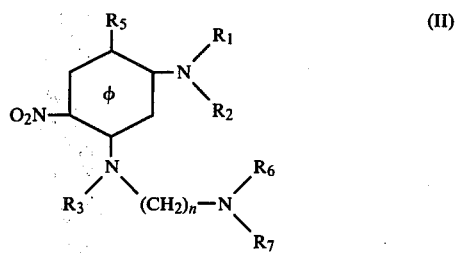

(II)

in which $R_1$, $R_2$, $R_3$, $R_4$, $R_5$, $R_6$, $R_7$ and n have the significances hereinbefore assigned thereto, and especially characterized by the fact that the compound having the formula (III):

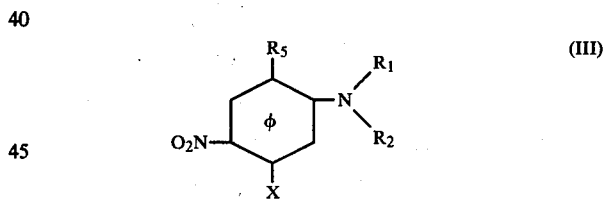

(III)

in which $R_1$, $R_2$ and $R_5$ have the significances hereinbefore assigned thereto and X represents a halogen atom or an $NO_2$ group, is reacted with an aliphatic corresponding to the formula (IV):

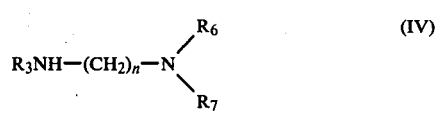

(IV)

in which $R_3$, $R_6$, $R_7$ and n have the significances hereinbefore assigned thereto, said reaction taking place preferably in the presence of a solvent such as pyridine.

A further object of the present invention is to provide a new process for preparing one category of the chemical compositions covered by the general formula (I) and corresponding to the formula (V):

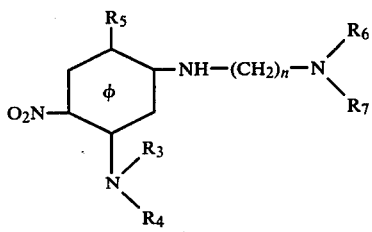

(V)

in which $R_3$, $R_4$, $R_5$, $R_6$, $R_7$ and n have the significances hereinbefore indicated provided $R_3$ and $R_4$ do not represent hydrogen, said process being essentially characterized by the fact that a composition corresponding to formula (VI):

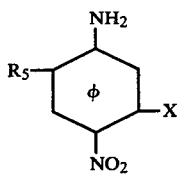

(VI)

in which $R_5$ has the significance hereinbefore indicated and X represents a halogen atom, is reacted with a secondary amine having the formula (VII):

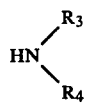

(VII)

in which $R_3$ and $R_4$ have the significances hereinbefore indicated; the primary aromatic amine is then converted into a monosubstituted arylsulfonamide by means of an aryl sulfochloride; and that a tertiary aliphatic halogenated amine having the formula (VIII):

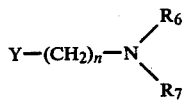

(VIII)

in which Y represents a halogen atom and $R_6$, $R_7$, and n have the significances hereinbefore indicated, is condensed on an alkaline or alkaline-earth derivative of said sulfonamide, after which the product obtained is subjected to acid hydrolysis, and then quaternized.

It should be noted that quaternization of a composition corresponding to formula (I) and having an extra-nuclear tertiary amine group is affected in the conventional way, utilizing a quaternizing agent such as an alkyl or aryl halide or methyl sulfate, in the presence of a solvent.

Preferred quaternizing agents include methyl chloride, methyl iodide, ethyl bromide, phenylchloride benzyl chloride, etc. which produce water soluble quaternary ammonium salts.

Yet another object of the present invention is to provide a hair coloring composition essentially characterized by the fact that it contains at least one dye responding to formula (I) or at least one of the corresponding quaternary compounds.

The coloring compositions according to the present invention make it possible to produce an intense yellow, slightly greenish shade on hair treated therewith. It should be noted that dyes corresponding to formula (I) have a strong affinity for the keratinic fibers of human hair and that the hair coloring compositions which are based on these dyes are particularly resistant to shampooing, but do not color the scalp. Moreover, the shades do not change with the passage of time.

The said hair coloring compositions are simple aqueous solutions of the aforementioned dyes. No oxidizing agents need be added to develop the color when these coloring compositions are used. Various conventional ingredients commonly used in hair dyeing compositions, such as organic solvents, thickening agents, detergents, perfumes, and lacquers, may be added to the hair coloring compositions in question.

The time during which these coloring compositions are left in contact with the hair may be varied within broad limits, but is preferably between 5 and 30 minutes. The temperature at which these compositions are applied may also be varied, but in most cases, they are preferably used at room temperature. The concentration of the dye in the hair coloring solutions may be substantially varied, but this concentration is preferably between 0.01% and 3%.

The coloring compositions according to the invention have, in general, a pH value between 4 and 10, and preferably between 7 and 9. Their pH may be adjusted by using as an alkali either plain ammonia, or any organic base such, for example, as an alkyl amine, an alkanol amine, or a heterocyclic amine.

It should be noted that the new dyes according to the invention may be mixed with each other and may also be mixed with other dyes, whether nitro dyes, azo dyes, anthraquinone dyes, or any of the other types of dye conventionally used for dyeing hair.

It should also be noted that dyes according to formula (I) may also be used for other than cosmetic purposes. In fact, the presence of a primary, secondary or tertiary extra-nuclear aliphatic amine group in the molecule of formula (I) imparts thereto a very substantial potential reactivity which can be put to good use in various synthesizing processes without being adversely affected by the reactivities of the nuclear amines, which are greatly reduced by the presence of a nitro group, whether ortho or para.

The invention also relates to a method of applying hair coloring solutions to the hair, which method comprises the steps of impregnating the hair with a coloring solution which is left in contact with the hair for 5 to 30 minutes, and then rinsing and drying the hair.

Described below by way of non-limiting illustration of the invention are several examples of preparation and use of these dyes.

EXAMPLE I

Preparation of 1-methyl,2-amino, 4-γ-dimethylamino-propyl-amino 5-nitro, benzene There is heated for 8 hours at reflux, 0.1 mol of 1-methyl, 2-amino, 4-chloro, 5-nitro, benzene, (that is, 18.65 g) in 0.4 mol of N,N-dimethyl-propylene-diamine, (that is 40.8 g) in the presence of 40 cm3 of pyridine. The greater part of the pyridine and dimethyl-propylene-diamine is expelled under vacuum, poured over dilute hydrochloric acid, the insoluble part is dried and the filtrate is alkalized with sodium hydroxide.

23 g of 1-methyl, 2-amino, 4-γ-dimethyl-amino-propylamino, 5-nitro, benzene almost pure are obtained which after recrystallization in alcohol melts at 123° C.

| Analysis | Calculated for C₁₂H₂₀N₄O₂ | Found |
|---|---|---|
| C % | 57.14 | 57.10 – 57.29 |
| H % | 7.93 | 7.91 – 7.79 |
| N % | 22.22 | 22.06 – 22.17 |

EXAMPLE II

Preparation of 1-methyl, 2-amino, 4-β-aminoethylamino, 5-nitro, benzene 0.1 mol of 1-methyl,2-amino,4-chloro, 5-nitro benzene (that is 18.65 g) is heated for 8 hours at reflux in 0.8 mol of ethylene-diamine hydrate, (that is, 65 cm3) in the presence of 40 cm3 of pyridine. The greater part of the pyridine and ethylene-diamine is expelled under vacuum, poured over dilute hydrochloric acid, the insoluble part is dried, and the filtrate alkalized with sodium hydroxide.

There is obtained 14.5 g of 1-methyl, 2-amino, 4-β-amino-ethylamino, 5-nitro, benzene, almost pure, which after recrystallization in alcohol, melts at 145° C.

| Analysis | Calculated for C₉H₁₄N₄O₂ | Found |
|---|---|---|
| C % | 51.43 | 51.21 – 51.33 |
| H % | 6.66 | 6.8 – 6.69 |
| N % | 26.66 | 26.58 – 26.35 |

EXAMPLE III

Preparation of methyl, γ-[N-(2-nitro, 4-methyl, 5-amino)phenyl]aminopropyl trimethylammonium sulfate 0.1 mol of 1-methyl, 2-amino, 4-γ-dimethyl-aminopropylamino, 5-nitro, benzene (that is, 25.2 g) is dissolved in 250 cm3 of nitrobenzene at air temperature; 0.11 mol (that is, 13.8 g) of methyl sulfate is added.

36.8 g of methyl, γ-[N-(2-nitro, 4-methyl, 5-amino)-phenyl]-aminopropyl trimethylammonium sulfate is obtained which melts with decomposition at 142° C.

EXAMPLE IV

Preparation of 1-amino, 3-γ-dimethylamino-propylamino, 4-nitro, benzene monohydrochloride For this preparation the reaction of the 3,4-dinitro acetanilide on an aliphatic dianine is utilized by taking advantage of the mobility of the $NO_2$ group located on the benzene nucleus in meta position of the acetylated amine. Then the amide function is hydrolyzed in a hydrochloric environment.

0.0137 mol of 3,4-dinitro, acetanilide (that is, 3.1 g) having 140° C. fusion point is heated for an hour at reflux in 0.3 mol of N,N-dimethyl-propylenediamine (that is, 30 g). The excess of aliphatic diamine is expelled under vacuum. The reactive mixture is poured into 100 cm3 of water. The 1-acetamino, 3,N,N-dimethylamino-propylamino, 4-nitro, benzene with ethyl acetate is extracted and the ethyl acetate is removed under vacuum. In this way 3.1 g of an oily product is obtained which is treated for a half-hour at reflux by 25 cm3 of a hydrochloric solution 3 times normal. After cooling and neutralization at pH = 6 by means of sodium hydroxide solution 5 times normal, 2.6 g of monohydrochloride of 1-amino, 3-γ-dimethylamino-propylamino, 4-nitro, benzene is dried, and after recrystallization in cold water, melts with decomposition at 280° C.

Analysis of the product obtained gives the following results:

| Analysis | Calculated for C₁₁H₁₉N₄O₂Cl | Found |
|---|---|---|
| C % | 48.09 | 47.99 – 48.18 |
| H % | 6.92 | 6.98 – 6.78 |
| N % | 20.40 | 20.26 – 20.25 |

EXAMPLE V

Preparation of 1-N,N-dimethylamino, 3-β-aminoethylamino-, 4-nitro, benzene 0.04 mol of 3,4-dinitro, N,N-dimethylaniline (that is, 8.4 g) is heated for an our at reflux in 0.8 mol of monohydrate ethylene-diamine (that is, 65 cm3). The reactive mixture is left overnight at ambient temperature and 7 g of crude 1-N,N-dimethylamino, 3-β-aminoethylamino, 4-nitro benzene is dried. This crude product, after having been carefully washed in water, is dissolved in half -normal hydrochloric acid. The hydrochloric solution is filtered in order to eliminate a small insoluble fraction; 6.2 g of the desired product is alkalized with a 10 times normal sodium hydroxide solution and dried. This product after recrystallization in isopropanol, melts at 108° C.

Analysis of the product obtained gives the following results:

| Analysis | Calculated for C₁₀H₁₆N₄O₂ | Found |
|---|---|---|
| C % | 53.57 | 53.36 – 53.52 |
| H % | 7.14 | 7.21 – 7.24 |
| N % | 25.00 | 24.93 – 24.99 |

EXAMPLE VI

Preparation of 1-N,N-dimethylamino, 3-γ-dimethylaminopropylamino, 4-nitro, benzene 0.227 mol of 3,4-dinitro, N,N-dimethylaniline (that is 48 g) is heated for 2 hours at reflux in 1.816 mol of N,N-dimethyl-propylenediamine (that is, 185 g). The excess of N,N-dimethyl-propylenediamine is removed under vacuum; the reactive mixture is poured into 600 cm3 of water, 56.2 g of the crude product is dried. This crude product, after having been carefully washed in water and dried, is recrystallized in cyclohexane. It melts at 79° C.

Analysis of the product obtained gives the following results:

| Analysis | Calculated for C₁₃H₂₂N₄O₂ | Found |
|---|---|---|
| C % | 58.65 | 58.57 – 58.74 |
| H % | 8.27 | 8.30 – 8.11 |
| N % | 21.05 | 21.02 – 21.06 |

EXAMPLE VII

Preparation of methyl, γ[N-(2-nitro, 5-dimethylamino)phenyl]aminopropyltrimethylammonium sulfate.

To a solution of 0.094 mol of 1-N,N-dimethylamino, 3-γ-dimethylaminopropylamino, 4-nitro, benzene (that is 25 g) in 250 cm3 of toluene is slowly added, without stirring, 0.094 mol of methyl sulfate (that is, 11.85 g).

The reactive mixture is left alone for two hours at air temperature and 35.1 g of the quaternized compound is dried. This compound, after recrystallization in alcohol, melts at 165° C.

Analysis of the product obtained gives the following results:

| Analysis | Calculated for $C_{15}H_{28}N_4O_6S$ | Found |
|---|---|---|
| C % | 45.91 | 45.95 – 46.07 |
| H % | 7.14 | 7.00 – 7.02 |
| N % | 14.28 | 14.40 – 14.36 |

EXAMPLE VIII

Preparation of monohydrochloride of 1-N,N-dimethylamino, 3-β-diethylaminoethylamino, 4-nitro, benzene 0.165 mol of 3,4-dinitro, N,N-dimethylaniline (that is, 35 g) are heated for an hour at reflux in 1.32 mol of N,N-diethylethylenediamine (or 153 g).

The excess of aliphatic diamine is removed under vacuum; the reactive mixture is poured into 450 cm3 of water. After having dried and carefully washed the crude product in water, it is dissolved in 150 cm3 of normal hydrochloric acid, filtered, and the pH of the filtrate is brought to 7 by means of a 5 times normal sodium hydroxide solution. 42 g of the monohydrochloride of 1-N,N-dimethylamino-3-β-diethylaminoethylamino, 4-nitro, benzene is dried, then after recrystallization in alcohol, melts with decomposition between 195° and 200° C.

Analysis of the product obtained gives the following results:

| Analysis | Calculated for $C_{14}H_{25}N_4O_2Cl$ | Found |
|---|---|---|
| C % | 53.08 | 53.20 – 53.17 |
| H % | 7.89 | 7.63 – 7.71 |
| N % | 17.69 | 17.82 – 17.70 |

EXAMPLE IX

Preparation of the monohydrochloride of 1-N,N-diethylamino, 3-γ-dimethylaminopropylamino, 4-nitro, benzene 0.074 mol of 3,4-dinitro, N,N-diethylaniline (or 17.7 g) are heated for an hour and a half at reflux in 0.6 mol of N,N-dimethylpropanediamine (or 60 g). The excess aliphatic diamine is removed under vacuum, the reactive mixture is poured into 100 cm3 of water and the awaited product is extracted with the help of isopropyl oxide. The solution of isopropyl oxide is saturated with gaseous hydrochloric acid and 18 g of monohydrochloride of 1-N,N-diethylamino, 3-γ-dimethylaminopropylamino, 4-nitro, benzene is dried, and after recrystallization in isopropanol, it melts with decomposition at 191° C.

Analysis of the product obtained gives the following results:

| Analysis | Calculated for $C_{15}H_{27}O_2N_4Cl$ | Found |
|---|---|---|
| C % | 54.16 | 54.57 – 54.69 |
| H % | 8.17 | 8.28 – 8.05 |
| N % | 16.94 | 17.08 – 17.09 |

Preparation of 1methyl, 2-β-diethylaminoethylamino,4-dimethylamino, 5-nitro, benzene.

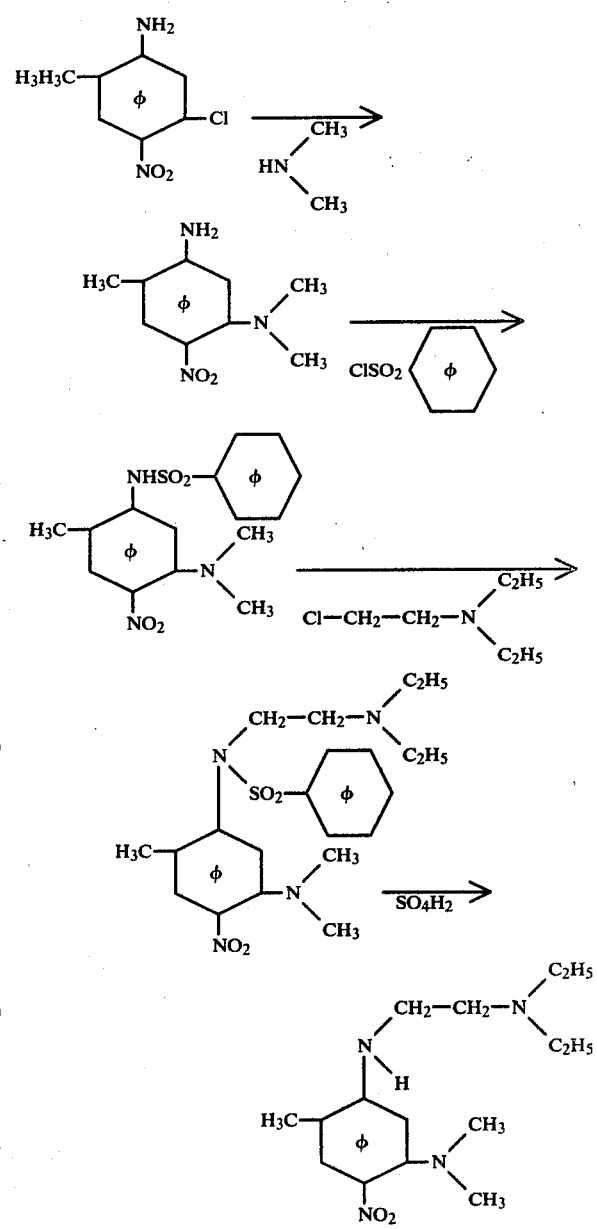

First Phase

Preparation of 1-methyl, 2-amino, 4-dimethylamino, 5-nitro-benzene 0.2 mol of 1-methyl, 2-amino, 4-chloro, 5-nitro, benzene (that is, 37.3 g) is heated for 16 hours at 125° C. with an aqueous solution at 40% of 1.6 mol of dimethylamine (that is, 180 g) in solution in 185 cm3 of absolute alcohol. After cooling 32 g of 1-methyl, 2-amino, 4- dimethylamino, 5-nitro, benzene crystallized in red needles is dried, this product after recrystallization in alcohol melts at 146° C.

Analysis of the product obtained gives the following results:

| Analysis | Calculated for $C_9H_{13}N_3O_2$ | Found |
|---|---|---|
| C % | 55.38 | 55.47 – 55.29 |
| H % | 6.66 | 6.59 – 6.51 |
| N % | 21.54 | 21.27 – 21.31 |

Second Phase

Preparation of 1-methyl, 2-benzenesulfonylamino, 4-dimethylamino, 5-nitro, benzene To a solution of 0.05 mol of 1-methyl, 2-amino, 4-dimethylamino, 5-nitro, benzene (or 9.75 g) in 60 cm3 of pyridine, slowly and while stirring, there is added at 45° C., 0.075 mol of benzene-sulfochloride (that is, 10 cm3). After the addition, the reactive mixture is held at 45° C. for two hours, then it is poured over 300 g of ice, is acidified up to pH 5 with a 5 times normal hydrochloric solution and the crude 1-methyl, 2-benzene-sulfonylamino, 4-dimethylamino, 5-nitro, benzene is dried. The crude product is redissolved in 50 cm3 of a 3 times normal sodium hydroxide solution. The sodium hydroxide solution is filtered: 1.5 g of the starting product insoluble in sodium hydroxide is recovered. Then 15 g of 1-methyl, 2-benzene-sulfonylamino, 4-dimethylamino, 5-nitro, benzene is obtained after neutralizing by hydrochloric acid and drying. It melts at 130° C.

Third Phase

Preparation of the 1-methyl, N-benzenesulfonyl, 2-N-β-diethylaminoethylamino, 4-dimethylamino, 5-nitro, benzene 0.02 mol of 1-methyl, 2-benzenesulfonylamino, 4-dimethylamino, 5-nitro, benzene (or 6.7 g) is dissolved in a boiling bath of 35 cm3 of dimethylformamide. 0.0206 mol of 95% potassium hydroxide (or 1.22 g) in solution in 7.7 cm3 alcohol is added, then quite rapidly 0.0204 mol of β-diethylaminoethylchloride (that is, 2.76 g) is added. The reactive mixture is kept for half an hour in a boiling water bath, poured into 150 cm3 of water, and the expected product is decanted under the form of orange oil which is purified by dissolving in 50 cm3 of a 5 times normal hydrochloric solution and by reprecipitation by means of a sodium hydroxide solution. Thus there is obtained 7 g of 1-methyl, 2-N-benzene sulfonyl-N-β-dimethylaminoethylamino, 4-dimethylamino, 5-nitro, benzene.

Fourth Phase

Preparation of 1-methyl, 2-N-β-diethylaminoethylamino, 4-dimethylamino, 5-nitro, benzene Slowly, while stirring, 0.06 mol of 1-methyl, N-benzenesulfonyl, 2-N-β-diethylamino-ethylamino, 4-dimethylamino, 5-nitro, benzene (or 29.6 g) is introduced into 70 cm3 of concentrated sulfuric acid between 0° and 5° C. The reactive mixture is let alone for four hours at 0° C.; then it is poured over 500 g of ice, is alkalinized with a 4 times normal sodium hydroxide solution, the expected product is extracted by means of ethyl acetate and the solvent is removed under vacuum. The oily residue is made into a solution in 60 cm3 of ethyl acetate. After having saturated the iced alcoholic solution with dry gaseous hydrochloric acid, 20 g of dihydrochloride of 1-methyl, 2-N-β-diethylaminoethylamino, 4-dimethylamino, 5-nitro, benzene is dried, and melts with decomposition at 180° C. The base, separated from its hydrochloride in the customary fashion, is an orange oil.

EXAMPLE XI

Preparation of methyl, β-[N-(3-dimethylamino, 4-nitro, 6-methyl)phenyl]-aminoethyl, methyldiethylammonium sulfate This quaternary compound is prepared by quaternization with methyl sulfate from the compound obtained as indicated in the example X.

0.049 mol of 1-methyl, 2-N-β-diethylaminoethylamino, 4-dimethylamino, 5-nitro, benzene (or 14.5 g) is dissolved in 120 cm3 of chlorobenzene at air temperature. 8 cm3 of methyl sulfate is slowly added while stirring and the reactive mixture is left for twenty hours at ordinary temperature. 18 g of the awaited quaternary is dried, and melts with decomposition at 153° C.

Analysis of the product obtained gives the following results:

| Analysis | Calculated for $C_{17}H_{32}N_4SO_6$ | Found |
|---|---|---|
| C % | 48.58 | 48.65 – 48.75 |
| H % | 7.61 | 7.84 – 7.78 |
| N % | 13.34 | 13.09 – 13.30 |

EXAMPLE XII

The following solution is prepared:
1 methyl, 2-amino, 4-γ-dimethylamino-propylamino, 5-nitro, benzene: 0.2 g
lauric alcohol condensed with 10.5 mol of ethylene oxide: 4 g
water, q.s.p.: 100 cm3
This solution has a pH of 9. It is applied to 100% white hair for ten minutes at ordinary temperature. Then the hair is rinsed and shampooed; a yellow shade is obtained.

EXAMPLE XIII

The following solution is prepared:
methyl, γ-[N-(2-nitro, 4-methyl, 5-amino)-phenyl]aminopropyl trimethylammonium sulfate: 1.9 g
lauric alcohol condensed with 10.5 mols of ethylene oxide: 5 g
$CO_3Na_2$ two times normal q.s.p.: pH=10
Water q.s.p.: 100 cm3
This solution is applied for 10 minutes on 100% white hair at ordinary temperature. Then the hair is rinsed and shampooed; a yellow shade is obtained, more sustained (lasting) then in Example XII.

EXAMPLE XIV

The following solution is prepared:
1-methyl, 2-amino, 4-γ-aminoethylamino, 5-nitro, benzene: 0.25 g
lauric alcohol condensed with 10.5 mols of ethylene oxide: 5 g
Water q.s.p.: 100 cm3
This solution is applied on 100% hair for 10 minutes. After rinsing and shampooing a very strong yellow green is obtained.

EXAMPLE XV

The following solution is prepared:
1-methyl, 2-amino, 4-β-aminoethylamino, 5-nitro benzene: 0.042 g
dihydrochloride of 1-N-β-aminoethylamino, 2-nitro, 4-N'-di-β-hydroxyethylamino, benzene: 0.252 g
lauric alcohol condensed with 10.5 mols of ethylene oxide: 4 g
$CO_3Na_2$ twice normal q.s.p.: pH=9
Water, q.s.p.: 100 cm3.

This solution is applied for 10 minutes on 100% white hair. After rinsing and shampooing a chestnut brown is obtained.

EXAMPLE XVI

The following solution is prepared:
1-methyl, 2-amino, 4-γ-dimethylaminopropylamino, 5-nitro, benzene: 0.025 g
dihydrochloride of 1-N-β-aminoethylamino, 2-nitro, 4-N'-di-β-hydroxyethylamino, benzene: 0.288 g
lauric alcohol condensed with 10.5 mols of ethylene oxide: 4 g
$CO_3Na_2$ twice normal q.s.p.: pH=7
Water, q.s.p.: 100 cm3

This compound is applied to 100% white hair for 15 minutes. The hair is rinsed and shampooed. A light gray beige is obtained (light natural gray).

EXAMPLE XVII

The following solution is prepared:
methyl, γ-]N-(2-nitro, 4-methyl, 5-amino)-phenyl-]aminopropyl trimethylammonium sulfate: 0.266 g
monohydrobromide of 1-N-methylamino, 2-nitro, 4-N'-β-aminoethylamino, benzene: 0.435 g
lauric alcohol condensed with to 10.5 mols of ethylene oxide: 1.5 g
$CO_3Na_2$ twice normal q.s.p.: pH=9
Water, q.s.p.: 100 cm3.

This compound is applied to hair of light chestnut to dark blond; it is left for 10 minutes; then hair is rinsed and washed. A strong mahogany chestnut is obtained.

EXAMPLE XVIII

The following coloring compound is prepared:
1-N,N-dimethylamino, 3-β-aminoethylamino, 4-nitro, benzene: 0.2 g
lauric alcohol condensed with 10.5 mols of ethylene oxide: 2 g
5% solution of citric acid, q.s.p.: pH=7
Water q.s.p.: 100 g This compound is applied to dark blond hair; it is left to act for 10 minutes, the hair is rinsed and washed. A bronze reflection is obtained.

EXAMPLE XIX

The following coloring compound is prepared:
1-N,N-dimethylamino, 3-γ-dimethylamino-propylamino, 4-nitro, benzene: 0.40 g
lauric alcohol condensed with 10.5 moles of ethylene oxide: 2 g
5% solution of citric acid, q.s.p.: pH=7
Water, q.s.p.: 100 g.

This solution is applied to chestnut hair, it is left for 10 minutes, rinsed and washed. A golden chestnut is obtained.

EXAMPLE XX

The following coloring solution is prepared:
methyl, γ-[N-(2-nitro, 5-dimethylamino)phenyl]-amino-propyltrimethylammonium sulfate: 0.37 g
lauric alcohol condensed with 10.5 mols of ethylene oxide: 2 g
sodium carbonate twice normal solution, q.s.p.: pH=9
Water, q.s.p.: 100 g.

This compound is applied to light chestnut hair; it is allowed to act for 10 minutes, rinsed and washed by shampooing. A dull folg reflection is obtained.

EXAMPLE XXI

The following coloring solution is prepared:
1-N,N-dimethylamino, 3-γ-dimethylamino-propylamino, 4-nitro, benzene: 0.23 g
monohydrobromide of 1-N-methylamino, 2-nitro, 4-N'-β-aminoethylamino, benzene: 1.16 g
lauric alcohol condensed with 10.5 mols of ethylene oxide: 1 g
sodium carbonate twice normal solution, q.s.p.: pH=9
water; q.s.p.: 100 g This solution is applied to light chestnut hair; it is left for 10 minutes, rinsed, and shampooed. A mahogany chestnut is obtained.

EXAMPLE XXII

The following coloring solution is prepared:
1-N,N-dimethylamino, 3-β-aminoethylamino, 4-nitro, benzene: 0.04 g
monohydrobromide of 1-N-β-aminoethylamino, 2-nitro, 4-N',N'-β-hydroxyethylamino, benzene: 0.27 g
lauric alcohol condensed with 10.5 mols of ethylene oxide: 2 g
citric acid, 5% solution, q.s.p.: pH=7
water, q.s.p.: 100 g.

This solution is applied to 100% white hair; it is left for 15 minutes, rinsed, and shampooed. A flat ash blond is obtained.

EXAMPLE XXIII

The following coloring solution is prepared:
methyl, γ-]N-(2-nitro, 5-dimethylamino)phenyl]-amino-propyltrimethylammonium sulfate: 0.20 g
monohydrobromide of 1-N-methylamino, 2-nitro, 4-N'-β-aminoethylamino, benzene: 0.35 g
lauric alcohol condensed with 10.5 mols of ethylene oxide: 4 g
sodium carbonate, twice normal solution, q.s.p.: pH=7
water, q.s.p.: 100 g This mixture is applied to light chestnut hair; it is left for 5 minutes, rinsed, and washed. A light chestnut with slight violine light is obtained.

EXAMPLE XXIV

The following coloring solution is prepared:
monohydrochloride of amino-1,3-γ-dimethylamino-propylamino, 4-nitro, benzene: 0.23 g
lauric alcohol condensed with 10.5 mols of ethylene oxide: 3 g
sodium hydroxide solution, 5 times normal, q.s.p.: pH=7.5
water, q.s.p.: 100 g.

This mixture is applied to light chestnut hair; it is left for 10 minutes, washed, and rinsed. A light golden chestnut is obtained.

EXAMPLE XXV

The following coloring solution is prepared:
monohydrochloride of 1-N,N-diethylamino, 3-γ-dimethylaminopropylamino, 4-nitro, benzene: 0.26 g
lauric alcohol condensed with 10.5 mols of ethylene oxide: 3.5 g
20% citric acid solution, q.s.p.: pH=8
water, q.s.p.: 100 g
This mixture is applied to light chestnut hair; it is left on for 10 minutes, rinsed and washed. A bronze high light is obtained.

EXAMPLE XXVI

The following coloring solution is prepared:
monohydrochloride of 1-N,N-diethylamino, 3-γ-dimethylaminopropylamino, 4-nitro, benzene: 0.05 g
monohydrobromide of 1-N-methylamino, 2-nitro, 4-N'-methyl-N'-β-aminoethylamino, benzene: 0.20 g
lauric alcohol condensed with 10.5 mols of ethylene oxide: 2.5 g
sodium carbonate, twice normal solution, q.s.p.: pH=8
water; q.s.p.: 100 g.
This mixture is applied to 100% white hair; it is left on for 15 minutes, rinsed and washed by shampooing. A light mahogany is obtained.

EXAMPLE XXVII

The following coloring solution is prepared:
monohydrochloride of 1-N,N-dimethylamino, 3-β-diethylaminoethylamino, 4-nitro, benzene: 0.32 g
lauric alcohol condensed with 10.5 mols of ethylene oxide: 4 g
sodium carbonate, twice normal solution, q.s.p.: pH=7
water, q.s.p.: 100 g.
This mixture is applied to light chestnut hair; it is left for 10 minutes, rinsed, and washed by shampooing. A dull gold light is obtained.

EXAMPLE XXVIII

The following coloring solution is prepared:
monohydrochloride of 1-N,N-dimethylamino, 3-β-diethylaminoethylamino, 4-nitro, benzene: 0.062 g
monohydrobromide of 1-N-β'-aminoethylamino, 2-nitro, 4-N',N',-β'-hydroxyethylamino, benzene: 0.188 g
sodium carbonate, twice normal solution, q.s.p.: pH=7
water, q.s.p.: 100 g.
This solution is applied to 100% white hair; it is left for 15 minutes, rinsed and shampooed. An ash blond is obtained.

EXAMPLE XXIX

The following coloring solution is prepared:
methyl, β-[N-(3-dimethylamino, 4-nitro, 6-methyl)-phenyl]-aminoethyl, methyldiethylammonium sulfate: 2 g
lauric alcohol condensed with 10.5 mols of ethylene oxide: 5 g
$CO_3Na_2$, twice normal, q.s.p.: pH=10
water, q.s.p.: 100 cm3
This solution is applied for 10 minutes to 100% white hair at ordinary temperature. Then the hair is rinsed; it is washed by shampooing; a sustained yellow shade is obtained.

EXAMPLE XXX

The following coloring solution is prepared:
methyl, β-[N-(3-dimethylamino, 4-nitro, 6-methyl)-phenyl]-aminoethyl, methyldiethylammonium sulfate: 0.067 g
dihydrochloride of 1-diethylaminoethyl-amino, 2-nitro, 4-N,N-dihydroxyethylamino, benzene: 0.328 g
iso-octylphenyl-polyethoxy-ethanol: 4 g
water; q.s.p.: 100 g
This mixture is applied to 90% white hair; it is left for 15 minutes; it is washed and rinsed. A light chestnut is obtained.

Other preferred illustrative compounds of this invention include:

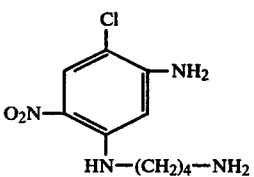

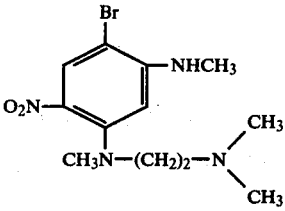

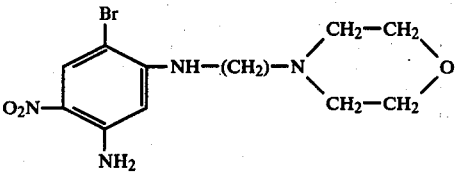

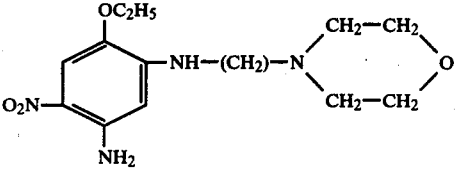

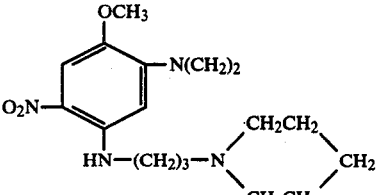

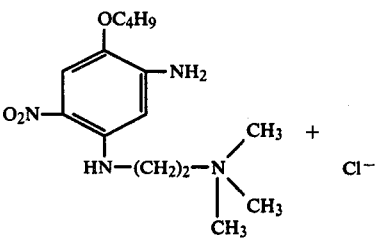

-continued

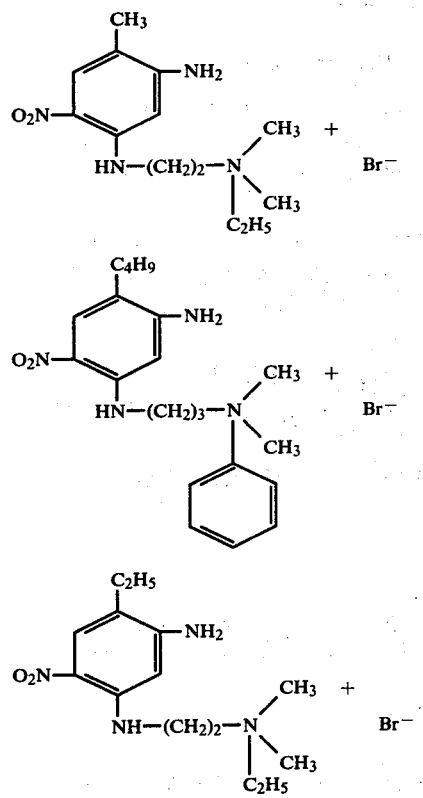

All of the disclosed substitute groups produce dyes that are suitable for dyeing live human hair.

What is claimed is:

1. A water soluble hair dye tertiary extra nuclear amine quaternary ammonium salt of a compound having the formula

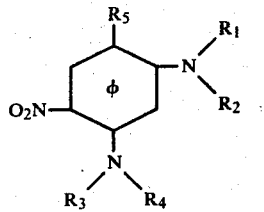

in which $R_1$, $R_2$, $R_3$, $R_4$ are selected from the group consisting of hydrogen, lower alkyl having 1–4 carbon atoms and tertiary extra nuclear amine having the formula

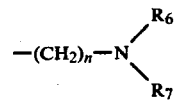

in which $R_6$ and $R_7$ are selected from the group consisting of lower alkyls having 1–4 carbon atoms, n represents a number between 2 and 6, a single one of the four $R_1$, $R_2$, $R_3$, $R_4$ representing said

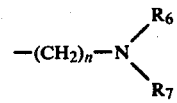

and $R_5$ is selected from the group consisting of hydrogen, lower alkyl having 1–4 carbon atoms, halogen and lower alkoxy having 1–4 carbon atoms.

2. A compound of claim 1, in which said compound is methyl-γ-[N-(2-nitro-4-methyl-5-amino)phenyl]-aminopropyl trimethyl ammonium sulfate.

3. A compound of claim 1, in which said compound is methyl-γ-[N-(2-nitro-5-dimethylamino)phenyl]-aminopropyltri-methyl ammonium sulfate.

4. A compound of claim 1, in which said compound is methyl-β-[N-(3-dimethylamino-4-nitro-6-methyl)-phenyl]-aminoethyl-methyldiethyl ammonium sulfate.

* * * * *

UNITED STATES PATENT OFFICE
CERTIFICATE OF CORRECTION

Patent No. 4,155,934            Dated May 22, 1979

Inventor(s) GREGOIRE KALOPISSIS and ANDREE BUGAUT

It is certified that error appears in the above-identified patent and that said Letters Patent are hereby corrected as shown below:

[30] Foreign Application Priority Data

December 3, 1965     Luxembourg......49,990

April 13, 1966       Luxembourg......50,894

October 19, 1966     Luxembourg......52,201

Signed and Sealed this

*Second* Day of *October 1979*

[SEAL]

*Attest:*

RUTH C. MASON
*Attesting Officer*

LUTRELLE F. PARKER
*Acting Commissioner of Patents and Trademarks*